United States Patent [19]

Andrews et al.

[11] 4,259,725
[45] Mar. 31, 1981

[54] CURSOR GENERATOR FOR USE IN COMPUTERIZED TOMOGRAPHY AND OTHER IMAGE DISPLAY SYSTEMS

[75] Inventors: Edward W. Andrews, Milwaukee; James E. Blake, New Berlin; Thomas W. Lambert, Dousman, all of Wis.

[73] Assignee: General Electric Company, Schenectady, N.Y.

[21] Appl. No.: 16,665

[22] Filed: Mar. 1, 1979

[51] Int. Cl.³ .................... G06F 3/14; G01N 21/00
[52] U.S. Cl. ........................ 364/521; 250/445 T; 340/709; 364/120; 340/724; 364/414
[58] Field of Search .................... 364/518–521, 364/120, 414, 200, 900; 340/709, 710, 724; 250/445 T; 358/183

[56] References Cited

U.S. PATENT DOCUMENTS

| | | | |
|---|---|---|---|
| 3,541,521 | 11/1970 | Koster | 340/710 |
| 3,593,310 | 7/1971 | Kievit | 364/900 |
| 3,610,902 | 10/1971 | Rahenkamp et al. | 364/521 |
| 3,729,129 | 4/1973 | Fletcher et al. | 340/709 |
| 3,883,861 | 5/1975 | Heartz | 340/709 |
| 4,116,444 | 9/1978 | Mayer et al. | 340/709 |
| 4,121,283 | 10/1978 | Walker | 340/709 |
| 4,129,859 | 12/1978 | Iwamura et al. | 340/724 |

OTHER PUBLICATIONS

Bennett et al., "Cursor Movement Control Circuitry"; IBM Tech. Discl. Bulletin; vol. 21, No. 3, Aug. 1978; pp. 1184–1186.

Primary Examiner—Errol A. Krass
Attorney, Agent, or Firm—Ralph G. Hohenfeldt

[57] ABSTRACT

A composite video signal waveform is fed through a video mixer and to a video monitor for displaying a raster scanned image on its screen. Signals are also fed through the mixer for causing a cursor having distinctive light intensity to be overlayed on the image. Programs for defining multiple cursors are stored in a readable memory. A microprocessor uses the programs for generating cursor parameters for each horizontal raster line and these are stored in a random access memory. A direct memory access controller responds to occurrence of each horizontal sync pulse by loading the cursor parameters for each corresponding raster line into counters which determine the starting point and end point of the cursor in that line or the width of the particular cursor line. During the interval representative of cursor line width, signals are fed through the mixer for altering the brightness intensity of the display. The random access memory is read out on a horizontal line-by-horizontal line basis so as to produce a whole cursor configuration between vertical blanking intervals. Operator interactive controls are provided for moving and angulating cursors.

14 Claims, 6 Drawing Figures

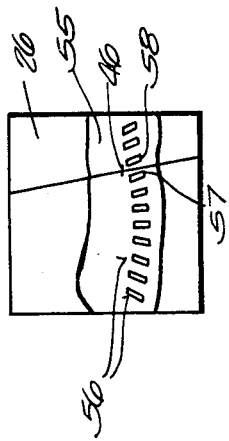
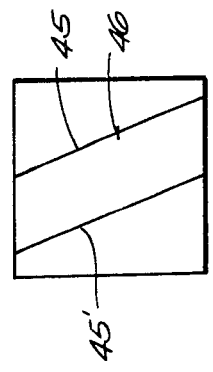
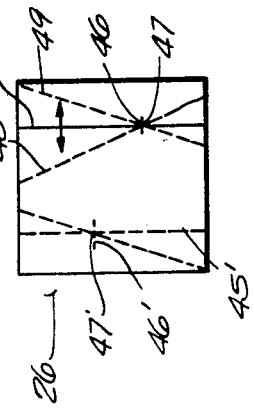
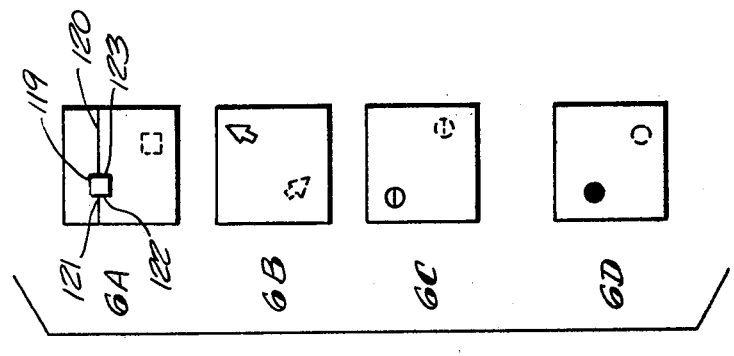
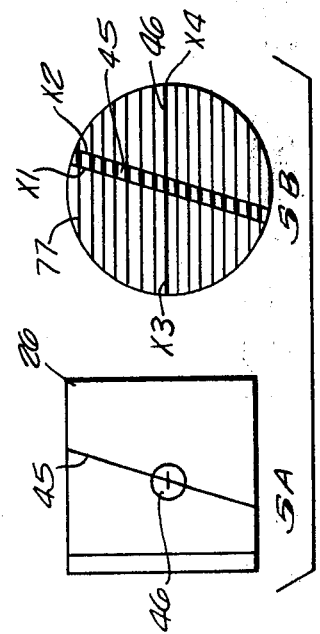

CURSOR GENERATOR FOR USE IN COMPUTERIZED TOMOGRAPHY AND OTHER IMAGE DISPLAY SYSTEMS

This invention relates to a system for generating cursors that are overlayed and movable on another image that is being displayed on a video display screen. The cursors are defined by brightening selected picture elements on the screen without destruction of the picture element data for the image which is being displayed. The new cursor generator is generally applicable to raster scanned video display systems, but for the sake of clarity which results from demonstrating its basic principles and utility in a concrete case, the generator will be described in connection with an x-ray computerized tomography system which uses a display controller or scan converter in the video display chain.

In the computerized tomography (CT) process, a body which is to be examined is disposed on a longitudinally translatable table. An x-ray source and a multicell x-ray detector are located on opposite sides of the body and are mounted for orbiting the body together. The x-ray beam is typically fan-shaped and is usually pulsed on and off as the source orbits and scans an axially thin layer in the body. During a scan, each detector cell produces an analog signal corresponding with the x-ray absorption of all body elements intervening between the source and detector cell for each of the x-ray bundles that make up the fan-shaped beam. A set of analog signals is thereby obtained from the detector cells as successive angular increments of orbital or rotational motion. The analog signals are converted to digital signals and subjected to computer processing. The computer executes an image reconstruction algorithm which results in a set of digital output signals that correspond in value with the x-ray absorption coefficients or transmissibility of each body volume increment in the scanned layer.

The digital output signals are ultimately sent to a video display controller where they are stored in memory as a matrix of picture elements (pixels) having the same X and Y coordinates as the body elements to which they relate. A typical matrix for producing images of diagnostic quality might have an array of $320 \times 320$ pixels.

As is well-known, the display controller converts the digital signal matrix to analog video signals for line-by-line display on a raster-scanned cathode ray tube screen or video monitor, thus enabling the reconstructed x-ray to be visualized as an axial view of the scanned body layer. The controller usually has an associated master clock which is the time base for producing the vertical and horizontal sync and blanking signals for the composite video signal which drives the monitor.

Usually during a diagnostic x-ray examination, x-ray absorption data is taken from several axially adjacent layers of the body. As soon as absorption data from a complete scan is obtained, it is processed in accordance with the reconstruction algorithm and the digital number matrix becomes available for facilitating image display. The data from the most recent body layer to be scanned is usually ready for enabling a display in a few seconds after the scan is completed. Data from the last layer scanned and from one or more layers previously scanned is often stored on magnetic disk to enable recall for video display as required by the operator or diagnostician.

Besides obtaining axial views of body layers as outlined above, modern CT machines are also often equipped for obtaining preliminary x-ray pictures of a body similar to the anterior-posterior views which are obtained using conventional radiographic film techniques. Some reasons for making a preliminary view are to enable the operator to determine the best angle for taking the axial layer views later and to determine the number of body layers that ought to be scanned to depict the entire anatomical region of interest, the object being to maximize clarity and diagnostic information in the axial views.

The somewhat conventional preliminary x-ray views are made by translating the body longitudinally through the x-ray beam while the x-ray source and detector are held in a fixed position. The x-ray source is usually pulsed on and off during body translation to provide a stopped motion effect. The absorption data obtained from the detector is processed in accordance with a suitable computer algorithm and, as in the case of making axial views, a matrix of digital signals is obtained which are used by the display controller to produce the preliminary view on the video monitor screen. The operator looks at the preliminary view and makes a judgment as to the number of axial layers which ought to be taken and as to the angle which the layers should be disposed at relative to the longitudinal or orbital axis of the scanner when the axial views are made subsequently.

As stated, the x-ray source and detector are mounted for orbiting in a common plane which can be tilted about a horizontal axis so the plane may be set in either angular direction from vertical to obtain axial views in planes which are at a vertical angle with respect to the nominally horizontal longitudinal axis about which the x-ray source and detector orbit during a scan.

One example of when the angle of the body layer is important is when the preliminary view shows that the anatomical part of primary interest is so located in the body that if vertical axial layers were taken through it, the full size and shape of the primary part would not be revealed even if several adjacent layers were scanned.

SUMMARY OF THE INVENTION

In accordance with the present invention, a movable cursor is displayed on the video screen in a manner which overlays it on the preliminary x-ray view that is presently on the display screen. The cursor helps the operator determine the scan layer boundaries, that is, the first and last layers which should be scanned in a sequence of layers and the proper angle of the layers relative to the longitudinal axis of the examination subject for getting maximum diagnostic information from the axial views which will be taken ultimately.

In accordance with another aspect of the invention, in a CT application where the angles and limits of axial layers are to be determined, the cursor preferably consists of a long straight line extending across the entire video display screen. The display tube is intensity modulated to make the cursor light bright or dark depending on whether the background image field is dark or light. For convenience, any cursor intensity will be called brightening in most usages herein. The line is vertical as initially displayed in the present example. The long line has a short bright line crossing it, similar to a crosshair cursor, such that the point at which the two lines cross serves as a pointer or reference point and is a virtual center of rotation for the long line in this example of the many different kinds of cursors that can be produced with the cursor generator. The point of intersection is called an isocenter because, in accordance with the invention, the point of cursor rotation or angulation does not shift even though a long straight cursor line is being rotated on the display of the preliminary view.

Operator interactive controls are provided for enabling the operator to move the long cursor line, or any other preselected cursor configuration, optionally left and right on the screen and to move the crossline (hereafter called a tick) up and down on the long line. The interactive controls can also be used to position the isocenter at a point where rotation of the line is to occur without translation of the isocenter. The operator can rotate the line to place it at the angle at which the axial layer views are to be taken. The CT system host computer reads the cursor angle and displays to the operator the positive or negative angle to which the scanner should be tilted to obtain correspondingly angulated axial views of the body layers.

The new cursor generator is applicable to CT systems, and to other image display systems which use display controllers or scan converters as they are sometimes called. Moreover, the cursor generator can be used with any raster scanned video system, whether or not it employs a display controller. In any case it is only necessary to use a video signal mixer for combining the ordinary video signals and the cursor generating signals which are then inputted to the display monitor together.

Besides enabling display of straight line cursors as described above, the new cursor generator can be easily programmed to recall and display a wide variety of cursor configurations or patterns such as pointers arrows, stars, circles, rectangles, asterisks, crosses, body shapes and the like and the cursors can be movable on the screen without destruction of any of the picture elements comprising the basic image that is being displayed.

Briefly stated, the new cursor generator is based on a microprocessor. Data for defining one or several different cursor configurations for simultaneous or individual display is loaded in or stored in any suitable memory such as a randon access memory (RAM) or a read-only memory (ROM) or a programmable read-only memory (PROM) which is coupled to the microprocessor through address and data buses. Each cursor configuration is defined by lines composed of one or more pixel elements in width in the horizontal or X direction on the display screen. Digital counters are used to set the point in each horizontal raster line point at which brightening of the pixels is to be started to start writing a horizontal component of a cursor line and to set the number of pixels which determines the width of the cursor line for each horizontal raster line. A vertical dimension or a line other than horizontal can be made up of brightened pixels on successive horizontal scan lines of the video display. It is, of course, the electron beam of the video monitor cathode ray tube that is modulated to high brightness in coincidence with occurrence of cursor pixels along successive horizontal raster scan lines.

The program for a particular cursor configuration desired may be called up by the microprocessor upon signal from a host computer (CPU) or by any other suitable selection means. In a straight line cursor application as was previously mentioned, a straight vertical line with a tick mark will appear when the corresponding program is called. The operator uses a trackball control, which is one of the illustrative operator interactive controls for positioning the vertical line and, particularly, the point of intersection of the tick mark (the isocenter) where the operator wants it. The operator then uses the other interactive device, a rotary control in this example, to rotate the vertical line angularly about the isocenter. The cursor can be angulated and translated in any order of events or at the same time. Control is wholly independent of the CPU or anything else at this time.

Advantages of using the new cursor generator, especially in a CT system, are: (1) fewer x-ray scans are required since the preliminary view and cursor data allow rapid localization of the region of primary interest in the body and the tilt angle of the orbital x-ray scanner can be accurately determined for the first scan based on the preliminary x-ray view and cursor data; (2) lower x-ray dose to the patient is achieved because the number of scan can be minimized; (3) rapid and accurate scan parameter determinations can be made based on operator interactive cursor location; (4) minimization of procedure time is achieved so equipment utilization is improved; (5) greater cursor pattern versatility is obtained due to microprocessor generated cursor parameter data; (6) the system can be expanded easily to support multiple cursors; (7) no limitation is set on cursor pattern size or shape except screen size; (8) cursor X-resolution is easily increased above that of the other image and graphics resolution; (9) high flexibility in passing operator related data to and from other elements of the display systems such as the host computer is achieved due to programmability of the cursor microprocessor; (10) cursor generation and operation are substantially independent of other processors such as the host CPU; (11) the cursors are non-destructive overlays of the image and graphic displays; (12) many cursor patterns are possible with a single hardware design; and, (13) the cursor generator design can be used to supply limited overlay graphics and figures for display controllers in a variety of image display systems that use display controllers.

Unique structural features of the invention are: (1) use of a random access memory (RAM) for the cursor counter data source; (2) use of a microprocessor to generate RAM-based cursor defining parameters; (3) use of a direct memory access (DMA) controller operating at video raster horizontal line rate to effect data transfer from RAM to the cursor starting position and cursor end or width counters; and, (4) use of position and width counter arrangements as opposed to position-only approaches to cursor generation.

How the above advantages and distinctive structural features of the cursor system are achieved will be evident in the ensuing more detailed description of a preferred embodiment of the invention which will now be set forth in reference to the drawings.

DESCRIPTION OF THE DRAWINGS

FIG. 2 is a view of a display screen on which one type of cursor is being displayed;

FIG. 3 shows a display screen on which two cursors are simultaneously displayed;

FIG. 4 shows a display screen on which a preliminary view of a body is displayed and wherein a cursor is set at an angle at which the operator desires to take axial views of body layers;

FIG. 5 are some diagrams which are useful for explaining how resolution of the cursor lines can be improved; and FIG. 6, composed of parts 6A-6D, show display screens with various kinds of cursor configurations overlaid on them.

DESCRIPTION OF A PREFERRED EMBODIMENT

Figure 1:
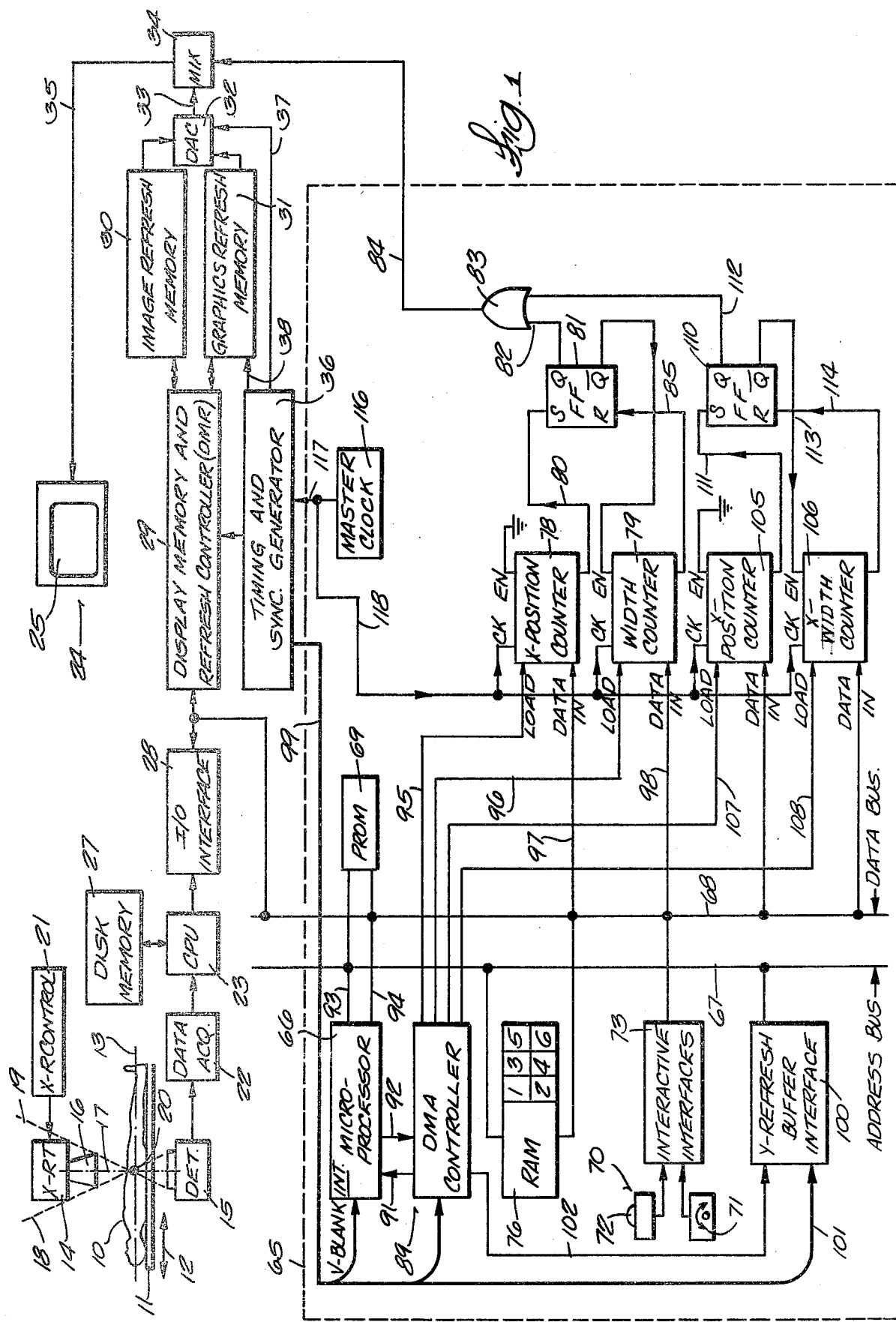
FIG. 1 is a block diagram showing the basic features of a computerized tomography system, its image display system in combination with the new cursor generating system.

Referring to FIG. 1, the conventional parts of a computerized tomography system will be described first to provide an environment for illustrating one application of the new cursor generator.

At the top of FIG. 1, a patient undergoing examination in a computerized tomography (CT) machine is designated by the reference numeral 10. The patient is supported on an x-ray permeable table top 11. The table is translatable, on command, in the longitudinal direction and bidirectionally as suggested by the arrow marked 12. The longitudinal axis is represented by the dashed line 13. An x-ray tube, (X-RT) 14, is located on one side of patient 10 and a multicell x-ray detector, (DET) 15, is located on the diametrically opposite side of the patient from the x-ray tube. The x-ray tube 14 has a collimator 16 coupled to its x-ray exit port for defining an axially thin fan-shaped x-ray beam which is projected through the patient during a tomographic scan. The center line of the x-ray beam is represented by the dashed line 17 which is vertical at the present time as shown. The fan-shaped beam diverges in laterally opposite directions in FIG. 1 and has a layer thickness, typically, of about 1 centimeter measured along the longitudinal axis 13.

It will be understood that the x-ray tube 14 and detector 15 are mechanically coupled so that they can orbit around the patient and x-ray table about longitudinal axis 13 during the axial body layer scanning process. The tube and detector run on a mounting in a gantry, not shown, which mounting is normally vertical as is the plane in which the x-ray tube and detector orbit. The mounting can be tilted away from vertical so that the tube and detector can orbit in any angulated planes between the ones represented by the dashed lines 18 and 19. Typically, the included angle between planes 18 and 19 is limited to about 30 degrees of tilt, that is, 15 degrees in either direction from vertical. It is desirable that the tilt be isocentric, that is, about a predictable fixed point or laterally extending axis such as where the planes 18 and 19 and vertical lines 17 intersect with the longitudinal axis 13 at the isocentric point marked 20. A suitable gantry mechanism, not shown, on which the x-ray tube 14 and detector 15 are mounted for orbiting and tilting is shown in detail in A. L. Kelman's U.S. Pat. No. 4,115,695 which is assigned to the assignee of the present application.

The x-ray tube power supply and pulse control is symbolized by the block 21. It is operative to pulse the x-ray tube 14 on and off while an orbital scan of each longitudinally adjacent body layer is being made. Pulsing the x-ray tube has the effect of stopping motion since the pulses are very frequent but of short duration.

As indicated earlier, two different types of x-ray scans are made with the CT machine. One is to obtain data for reconstructing an axial view of a layer of the body looking along axis 13. The other type of scan is longitudinal and produces a preliminary view of the body similar to that which would be obtained on a radiographic film that would be located approximately where detector 15 is located. Of course, the preliminary view is displayed on a cathode ray tube screen and not on any film. The scan for the preliminary view is made by advancing the patient through a pulsed x-ray beam along longitudinal axis 13 at a constant rate while the x-ray tube 14 and detector 15 are held in a fixed position. As indicated earlier, a preliminary view is generally made prior to making the axial scans to enable the operator to see some anatomical reference points which will aid in determining the angle at which the axial layer scans should be made and the number of layers that should be scanned.

A multicell detector which is suitable for use in the CT machine is described in detail in Shelley et al's U.S. Pat. No. 4,119,853 which is assigned to the assignee of this application. When making an axial scan, x-ray tube 14 and detector 15 may orbit through a complete circle. The respective cells in the detector 15 which are disposed along the leading edge of the fan-shaped beam produce a set of analog signals which are representative of x-ray absorption by the multiplicity of body volume elements that lie along the ray paths between the x-ray tube and detector. Thus there is a set of analog data signals for each angular increment of orbiting or rotation by the x-ray tube and detector. The process is symbolized by the block marked 22 which is further identified as a data acquisition means. The data resulting from respective axial layer scans and longitudinal scans for preliminary views is converted to separate sets of digital pixel data and used by a central processing unit or computer (CPU) which is symbolized by the block marked 23. CPU 23 is programmed to process the digital data and produce a matrix of data values that correspond, insofar as X,Y coordinates are concerned, with the X,Y coordinates of the body elements to which the absorption data relates. This data is ultimately used in a raster scan video monitor 24 for displaying an image 25 of a body layer on its screen 26. It will be understood, of course, that distinct algorithms are used for developing the data for reconstruction of the respective preliminary view scans and the axial scan views.

One of the views can be shown substantially in real time on monitor 24, that is, only after a few seconds which it takes for the CPU to execute the image reconstruction algorithm. The data for any previously taken axial or preliminary view scan may be stored in a disk memory 27 for recall at any time that the operator wants to display an image selected from this collection.

The host computer, CPU 23, communicates with the outside world through a multiport input/output (I/O) interface which is symbolized by the block 28. A display refresh and memory controller (DMRC) 29 of a known type is used to control display of images on the screen 25 of video monitor 24. DMRC 29 outputs digital data to an image refresh memory 30 and a graphics refresh memory 31 which store the matrix of data for the presently displayed x-ray images and any graphics that are displayed on the screen as commanded by the CPU 23 but these memories are not used to store cursor generating data. Memories 30 and 31 are read out or scanned on a horizontal line-by-horizontal line basis and, of course, each line is composed of pixel signals represented by the values of the data in each location of the matrix memories. This line-by-line data is converted to corresponding analog video signals in a digital-to-analog converter (DAC) represented by the block 32.

In accordance with the invention, the output from DAC 32 is supplied to one input 33 of a video signal mixer (MIX) 34. The output of the mixer 34 is supplied by means of a bus 35 to the video input of monitor 24. The horizontal and vertical sync and blanking pulses are, of course, added to the converted analog video waveform from a timing and sync generator 36 by way of a cable 37 as indicated. As indicated by the lines 37 and 38, the DMRC 29 and the graphic and image refresh memories 30 and 31 are all driven in synchronism from signals derived from the timing and sync generator 36. The master clock pulse generator, symbolized by the block marked 116 in FIG. 1, serves as the highest pulse rate time base of the system. Master clock 116 furnishes the clock pulse train, by way of line 117, to timing and sync generator 36 which divides the train as required to produce clock pulse trains for synchronous readout of the image refresh memory 30 pixels and the graphic refresh memory 31 pixels. For example, a horizontal line for the image or picture on the screen may, in this example, contain 160 pixels and there is a corresponding number stored in image refresh memory 30 for each line. A horizontal line for graphics may contain a different number of pixels such as 320 for good resolution and sharpness. Thus, the graphics pixel clock rate is two times the image pixel clock rate and, in this example, the master clock rate is four times the image pixel clock rate. The high rate master clock pulse train is also fed out on line 118 to some counters which are clocked at this high rate for the purpose of optimizing resolution of the cursor defining lines as will be discussed in detail later.

The background developed as of this juncture is for demonstrating that a composite video signal for graphics or an image or both is inputted to a video signal mixer 34 and outputted to a video monitor and that it is unconsequential, insofar as the new cursor generation method is concerned, whether the composite signal is obtained from a display controller system, a video camera or storage such as magnetic tape or disk. What remains to be explained is how the cursor producing signals are generated and also inputted to the mixer for display on the monitor screen.

Before describing the new cursor generator system in detail, some of the characteristics of one type, that is, of a straight line cursor with a straight tick mark used in a CT system will be discussed in reference to FIGS. 2–4. When the cursor is called for by the system to be described, a bright vertical line such as the line 45 in FIG. 2 will appear on the screen. The line has a horizontal crosshair or tick mark 46 on it which intersects with the vertical line at point 47. The cursor generator, as will be described, enables the operator to move the vertical cursor line 45 laterally of the screen such as to a position where it is shown in dash marks representing the line 45'. This is a bright line on the screen and does not destroy any information in the image on which it is overlaid. The cursor line 45 may also be tilted by the operator through a limited angle whose boundaries are indicated by the dashed lines 48 and 49. The angle limits ordinarily correspond with the angular limits of gantry tilt. When cursor line 45 is tilted through the angle included between lines 48 and 49, tilting or rotation occurs about isocentric point 47. The tick mark 46 is movable by the operator to establish the isocenter at any point 47' which the operator desires. Rotation or tilting will always be about isocenter point 47 or 47', for example. Horizontal cursor lines may also be generated for some purposes.

FIG. 4 illustrates a use of the cursor for determining the angle at which the plane of the orbitally scanning x-ray tube and detector should be tilted to view a part of the anatomy advantageously. In FIG. 4, a longitudinally extending preliminary x-ray view 55 is depicted on video display screen 26. The spinal column 56 can be visualized. By way of example, the operator or diagnostician may be interested in getting an axial layer view of cartilage or disks between two vertebrae 57 and 58. The previously angulated cursor line 45 and its tick mark, intersecting at point 46, are also being displayed on the screen. The operator would rotate line 45 about isocenter point 47 to the angle in which cursor line 45 is shown in FIG. 4. The operator might decide to move the tick mark down to the point where the isocenter 47 is located between adjacent vertebrae 57 and 58 before rotation is made since this assures that cursor line 45 will be rotated into parallelism with the angulated planes of the vertebrae and further assures that the axial view of the body layer will be taken at the proper place and proper angle. This is but one example of use of a particular type of cursor which is especially useful in computerized tomography applications and is obtainable with the new cursor generator.

As mentioned briefly earlier, host CPU 23 reads out the angle of cursor line 45 and the location of isocenter 47 and the CPU displays data which indicates to the operator the angle to which the gantry, that is, the rotational plane of the x-ray tube and detector should be tilted to take an axial view perpendicular to the body layer plane of interest such as the angulated plane between the vertebrae.

By means which will be discussed later, several cursors may also be made to appear on display screen 26 at the same time with an image as illustrated in FIG. 3 where two straight line cursors are shown. The one cursor line 45 corresponds with its counterpart in FIG. 4 which was used for determining angle and location of the body layer of interest. The other cursor 45' in FIG. 3 may be independently generated for the purpose of setting the boundaries of the layers that are to be scanned. Cursor line 45' does not necessarily need a tick mark.

The manner in which cursors are generated will now be discussed in reference to FIG. 1. The new cursor generator lies within the boundaries of the dashed line rectangle marked 65. It includes a microprocessor 66 which is coupled to an address bus 67 and a data bus 68. A readable memory such as PROM 69 is also connected to address bus 67 and data bus 68. The PROM stores program data which enables the microprocessor to generate data for producing a variety of movable cursor configurations whenever it is requested to generate data for one or more cursors. In a commercial embodiment, a type Z-80 microprocessor 66 made by Zilog Corp. was used but other microprocessors could be used as well. The Z-80 is available from Mostek Corp. which designates it as Part No. MK3880.

The complete instruction set for software and timing diagrams for hardware are given in "Mostek Technical Manual for the MK3880 Central Processing Unit," dated August, 1976.

To enable the operator to position the vertical cursor line 45 on the display screen 26 and to enable moving the tick mark 46 up and down on the vertical cursor line to establish the isocenter 47 at a particular point, an operator interactive device constituting a trackball control 70 is used. The operator can tilt the vertical cursor line with the other interactive device, that is, with a rotatable control 71. The details of the trackball device are not shown since the characteristics of trackball controllers are well-known. One is described in more detail in co-pending application, Ser. No. 939,088, filed Sept. 1, 1978 which discloses another type of cursor generator. As is known, a trackball controller has a ball 72 mounted for universal rotation. The ball drives encoders, not shown, which produce one set of signals when the ball is turned in the X direction and another set of signals when the ball is turned in the Y direction. These signals can be interpreted to indicate the X and Y coordinates of a point on a video display, for example. The point of interest in this example is the isocenter point 47 where the tick mark 46 crosses the long vertical cursor line 45. Encoders in the trackball controller 70 produce data indicative of the X and Y coordinates of this point and this data is coupled by means of an interface unit 73 to the data bus 68 for being read out by microprocessor 66.

Rotatable control 71 is essentially a step switch which, in this example, is preferably rotatable in one degree steps to make the long cursor line 65 tilt at a corresponding angle. As indicated earlier, enough steps to encompass a 30° included angle is sufficient for CT applications of the cursor generator. Rotatable control 71 produces digital data representative of tilt angle values and couples the data to data bus 68 through a suitable interface unit in the interface block 73. This enables the microprocessor to read the angular setting of the rotary control 71. In fact, the microprocessor is constantly checking the setting of the interactive devices 70 and 71 in order to make a change in its output data that defines the cursor parameters whenever the interactive devices are operated.

A random access memory (RAM) 76 is coupled to the address and data buses 67 and 68. The parameters required for cursor generation, that is, the parameters or data indicating the position and width of the horizontal lines which comprise the cursor, is generated by the microprocessor program and stored in RAM 76. The number of locations of RAM required to store cursor parameter data is equal to the number of horizontal scanning lines used to present the raster scanned image on video display screen 26. By way of example, 320 locations of microprocessor RAM 76 are used to store X-position parameter data and 320 locations are used to store width parameter data.

Digital data which specifies the starting position for altering to bright or dark the picture elements on each horizontal video line on which a part of the cursor is written and also specifies the width of that line are the only parameters needed to define a cursor of any configuration. This can be seen in part A of FIG. 5 where a straight line cursor 45 with a tick 46 is shown. The region where the tick 46 intersects line 45 is encircled and shown in part B in magnified form. The horizontal raster scan lines are indicated by the fine lines 77. One or more pixel elements in each successive horizontal line may define the vertical line 45. Thus, each horizontal line, which is part of a brightened cursor line, can be defined by its starting point or $X_1$ coordinate and by the number of pixels or width of that line which terminates at coordinate $X_2$. Thus, by using starting location and width counters, which will be discussed, pixel counts can be made from the left edge of the display screen until the $X_1$ coordinate is reached on each raster line. Then the width counter counts pixels for the horizontal width or length of the cursor line and the video display tube is modulated bright until $X_2$ is reached. When the raster line is completed the same procedure is repeated for the next and ensuing horizontal lines. The tick mark 46 starts at coordinate $X_3$ and terminates at coordinate $X_4$. Its length is also specified by the width data stored in RAM for the horizontal line along which the tick mark extends.

Returning to FIG. 1, the microprocessor 66 reads the output from operator interactive devices 70 and 71 to get the operator input data and then proceeds to generate and store the 320 values, in this example, of starting position and width data for each horizontal line required to define the cursor pattern which has been selected.

For each cursor that is to be generated simultaneously, a block of memory locations must be reserved in RAM 76. Each block of memory is preferably divided into two partitions. One partition stores the position and width parameters for a cursor which is currently on display and the other stores the same data or new data which results from the operator using the interactive devices 70 and 71 to change the location of the tick mark or the vertical line or the angle of the line. In other words, complete data for a cursor in one position is stored in one partition and complete data for another cursor position is stored in another partition and the partitions are read out alternately. In RAM 76, for example, symbolized partitions 1 and 2 would be for one cursor, partitions 3 and 4 for another and partitions 5 and 6 for another and so forth. A single partition would be satisfactory for some cursor applications.

For each cursor that is to be displayed, at least a pair of digital integrated circuit counters are used. One counter is for starting the cursor pixel writing process on each horizontal raster line and the other counter is for stopping the process to thereby establish the horizontal width as represented by the series of bright pixels in the line. In this embodiment, one counter marked 78 in FIG. 1 is the X-position counter which is used to set the starting point for one or more cursor pixels on a raster line. The other marked 79 is the width counter X-position. Counter 78 is parallel loaded with the data specifying the X coordinate of the starting point of each horizontal line comprising a cursor coincident with occurrence of the horizontal blanking pulse for each line of the video display. Similarly, the data specifying the width for the particular horizontal cursor defining line which is to be written is parallel loaded into the width counter 79 immediately after the starting position counter is loaded. At the end of horizontal blanking, X-position or starting point counter 78 begins to count. When it reaches overflow, it produces a state change on its output line 80 which is delivered to the set pin S on a flip-flop 81. The Q output of flip-flop 81 then changes state, goes high for example, and delivers a corresponding signal by way of line 82 to a gate 83. The output of gate 83 is coupled by means of line 84 to mixer 34. In mixer 34, the logic high signal from the gate is mixed with the composite video signal for the currently existing horizontal line and writing of the cursor line begins. When flip-flop 81 is set by the signal from X-position counter 78, its $\bar{Q}$ pin goes from high to low and activates underflow width counter to begin counting to establish the width of the cursor line which has been determined by the data previously entered into the width counter. When width counter 79 reaches underflow, a change of state occurs on its output line 85 and this signal is delivered to the reset pin R of flip-flop 81. When reset occurs, the Q pin of flip-flop 81 goes low again and the signal to mixer 34 is terminated in which case the remainder of the horizontal scanning line is no longer intensified or brightened and the line displays the pixel content of the x-ray image which is being displayed. As suggested earlier, by inversion of the signals from gate 83, the cursor signals could be used to alter the display intensity so the cursor pixels go toward blackness instead of brightness.

Counting to obtain the start and end points for the cursor pixels in each horizontal raster line can be implemented with pairs of counters connected in a manner which differs from the above discussed arrangement. For example, two counters, not shown, can be adapted to count pixels for a horizontal cursor pixel series simultaneously. The first counter may reach the start point $X_1$ and then set a flip-flop, not shown, so the flip-flop will change its output state and feed through mixer 34 as before. When the second counter reaches the count that corresponds with the end point $X_2$ of the cursor pixel sequence it resets the flip-flop, thereby terminating the signal to the mixer so the remainder of the pixels in the line will not cause the display to be modulated to high brightness.

A direct memory access (DMA) controller 89 is used for presenting X or starting position parameters and width parameters to counters 78 and 79, respectively. In other words, part of the DMA controller's task is to coordinate the data load signals to the counters 78 and 79 and any others which may be used, with actual readout of cursor parameter data from RAM 76. There is a horizontal blanking signal input 90 to the DMA controller. Every time a horizontal blanking pulse is delivered to the DMA controller from the timing and sync pulse generator 36, the controller makes a DMA request of microprocessor 66 by way of an appropriate signal on line 91. When the microprocessor is ready, it returns a DMA acknowledge signal to the DMA controller 89 by way of a line 92. When the microprocessor has completed its present instruction cycle following a DMA request and acknowledgment, it stops what it is doing and sets its output lines 93 and 94, which connect to address bus 67 and data bus 78, in a high impedance state. The microprocessor then remains in a state of suspended animation until the DMA controller 89 terminates its DMA request. During the short time that microprocessor activity is suspended, data bus 68 is cleared for permitting transfer of digital data for the X-position and width parameters relative to the cursor for one horizontal line to counters 78 and 79, respectively. The first thing that happens during the horizontal blanking interval is that the data from RAM is placed on data bus 68. Counter load signals are then delivered sequentially by way of lines 95 and 96 to the load signal input pins of the position and width counters 78 and 79 and the data for a horizontal line is parallel loaded and latched. Thus, the data for one horizontal scan line is in the counters and they go through their counting sequence as described above. When the next horizontal blanking pulse is delivered to the DMA controller, the counter load procedure for the next horizontal scan line is repeated until the lowermost horizontal scanning line has been reached at which time a vertical retrace and blanking signal is delivered by the timing and sync generator 36 to an interrupt signal input pin (INT) on microprocessor 66. During the interrupt, a switch to the alternate memory partition in RAM 76 is made.

The RAM partition selection process is a microprocessor controlled function. When the microprocessor has completed generation of all the data for a complete cursor view, it is ready to switch partitions and feed the new cursor data to the RAM and counters. When the microprocessor receives this interrupt it sends out a partition select bit which is used in the RAM address.

Those skilled in the art will appreciate that the vertical blanking signal could be detected by polling instead of using it as an interrupt. For instance, the microprocessor could poll the source of the vertical blanking signals to determine if the display is entering vertical blanking and the microprocessor could send out a signal for switching RAM partitions in response to the vertical blanking condition occurring.

It will be evident that the RAM 76 has to be addressed for each line of cursor data retrieval and that the address has to be based on the current horizontal line being scanned in the video monitor under the control of display and refresh memory controller 29. That is, cursor parameter data retrieval has to be based on the Y or vertical position of the raster line being scanned by monitor 24 as it is writing the reconstructed x-ray image and graphics information on the monitor screen 25. The Y-position indication is derived from the timing and sync generator 36 for the display such that the actual Y location can be used as a portion of the address which is accessing the RAM 76. For controlling the display, of course, the sync generator has to generate horizontal and vertical sync and blanking pulses. It accesses its image refresh and graphics refresh memories 30 and 31 in terms of the X and Y coordinates of each image pixel stored in those memories. The position of each pixel on the display screen has specified X and Y coordinates. Hence, the counter chain which was mentioned earlier as being in the timing and sync generator 36 but is not shown, is being driven by the master clock 116 such that when the counter for the pixels in the X-direction overflows at the end of each horizontal scan line, the Y counter is incremented. When X counter overflows, the horizontal sync and blanking times are entered and retrace and indexing of the Y counter is performed. The Y counter overflows when the total number of scanning lines permissible on the display screen has been reached; that is, the bottom of the screen 25 has been reached. This provides a Y count value or address for telling the microprocessor RAM 76 which horizontal line is about to be scanned. Since the timing and sync generator 36 is producing Y addresses for display controller 29, these addresses can also be used to determine the horizontal line which is to be taken from RAM 76 in synchronism.

Thus, a Y refresh buffer interface 100 is provided. It is coupled with address bus 67. One input to Y refresh buffer interface 100 is a set of lines 101, taken from bus 99, which provide the Y memory address from the timing and sync generator 36. The Y refresh buffer 100 is simply a circuit which allows the RAM address to be imposed on the address bus 67. As indicated by the line 102, it is controlled by the DMA controller 89 such that during horizontal blanking when the bus is made available by the microprocessor, the Y address is put on the address bus as part of the component which is used to access RAM 36 for putting the cursor X-position and width parameters for that line on the data bus so they can be delivered to the data inputs of the counters 78 and 79 by way of buses 97 and 98. As stated, in the illustrated embodiment, when vertical blanking occurs, the microprocessor switches partitions in RAM 36 so that when the next sequence of addresses comes along the alternate partition of RAM memory will be accessed by the counters. RAM partitioning is not an absolute requirement for all types of cursors. It is a good feature, however, where it is desirable to avoid having the cursor data in RAM change until a complete cursor in a particular position on the screen is displayed.

It will be evident that the system is adaptable to producing several different or identical cursors simultaneously. For each additional cursor a set of locations in RAM must be allocated to accommodate all of the additional cursor parameters for all of the horizontal lines of the display. Another counter pair is also required the additional cursors so they can be displayed, independently of each other. In FIG. 1, an additional pair of X-position and width counters 105 and 106, respectively, are shown for this purpose. They are loaded by load pulse signals delivered over lines 107 and 108 from the DMA controller 89. One DMA controller can handle several cursors.

Counters 105 and 106 for a second cursor operate in the same way as the previously described counters 78 and 79. As before, the process involves signalling the microprocessor by any suitable control means to draw the program from PROM 69, or whatever readable memory is used, for generating the particular cursor. The microprocessor then develops the data for the new cursor parameters and sends it to the RAM locations reserved for this cursor during a blanking interval. Then when the RAM is addressed during occurrence of horizontal blanking pulses, the DMA controller will send load signals over its output lines 107 and 108 to the counters 105 and 106 in rapid sequence to parallel load the data from one of the partitions on a line-by-line basis into the counters. When the DMA controller completes transfer of X-position and width counter data to one set of counters for one cursor, it immediately continues with transferring data to the one or more additional sets of counters which are used for the other cursors. The horizontal blanking pulses are generally long enough to permit making many data transfers to the counters between their occurrences.

The second set of position and width counters 105 and 106, like the first set 78 and 79, set a flip-flop when the X or starting position pixel count is reached, and reset the flip-flop when the pixel count that determines the width is reached. The second flip-flop is marked 110. When X-position counter 105 underflows, flip-flop 110 is set via line 111 and its Q output goes high. Gate 83 is then turned on via line 112 to send a write cursor signal through mixer 34. When Q output goes high, the $\bar{Q}$ output of flip-flop 110 goes low and the state change is sent via line 113 to enable count down by width data counter 106. When it reaches underflow, indicating that the width or number of pixels for the cursor on the present horizontal has been determined, counter 106 sends a signal by way of line 114 to reset flip-flop 110 and gets it ready for the next horizontal scan line.

If a cursor pattern having two sides to it, such as the square cursor 119 in part A of FIG. 6, is to be produced, to pairs of X-position and width counters would be required as can be appreciated by considering what happens during each horizontal line such as on the one raster line marked 120. One X-position counter would reach underflow at the point marked 121. Its associated width counter would underflow when it determined the number of pixels for defining the width of the vertical line 122 on the left side of the square. At point 123 at the right side of the square, the X-position counter in the other pair would underflow and start to write brightened pixels until its associated width counter underflowed to thereby determine the width of the vertical line on the right side of the square. Generation of cursor shapes as in parts 6B–6D of FIG. 6 would be carried out in the same way.

From the foregoing description it should be evident that cursors having a variety of shapes can be produced with the new generator. Examples of some cursors which the microprocessor 66 can be programmed to produce are exhibited in FIG. 6, parts 6A–6D. Part 6A shows a movable cursor defined by a square. Part 6B shows a cursor in the form of an arrow. Part 6C shows a cursor comprised of crosslines encompassed in a circle. Part 6D shows a cursor which looks like a solid bright circle or disk. An implied earlier, the program for generating any of these and other cursor configurations may be stored in a memory such as PROM 69 for use by the microprocessor in generating corresponding data to be sent to RAM 76 for storage in an X,Y coordinate memory matrix. For every scan line there will be one or more X-position coordinates for delivery to the X-position counter and one or more bytes of width data for controlling the width of a line that outlines or composes a particular cursor configuration. Thus, many cursor patterns can be made available with the single hardware design encompassed within the cursor generator 65.

Another feature of the new cursor generator is that it facilitates automatic display of a second straight line cursor which is a substantial duplicate of the straight line cursor with the tick mark which was first called up and displayed. An example is shown in FIG. 3. Here the originally generated straight line cursor 45 is shown in an angulated position and is the result of a cursor obtained by use of the operator interactive controls 70 and 71. The host computer, CPU 23, has the proper software for being commanded to read out through its I/O interface 28 the X and Y coordinate parameters of the isocenter, that is, the point where the tick mark 46 intersects long cursor line 45 for the cursor currently being displayed. The host computer also reads the angle parameter for the long cursor line. It sends these parameters to the microprocessor 66 which then draws the straight line cursor program from memory 69 and loads RAM 76 locations accordingly.

For a moment it will appear to the operator that the two similar cursors are one because they are exactly superimposed. Then the operator is free to use the position interactive control 72 to move the first cursor 45 to the right or left while maintaining its angle constant. Cursor line 45' represents a typical position to which cursor line 45 has apparently been moved under operator control. Actually the second cursor stays coincident with where line 45 is located. The operator will locate cursor line 45' at one of the limits of the body layers which are to be scanned for axial views and parallel cursor line 45 becomes the other limit. CPU 23 is programmed to read out the cursor location parameters and to calculate the number of adjacent approximately one centimeter thick body layers and, hence, the number of x-ray scans which are required to cover the body region between the parallel cursor lines 45 and 45'.

Referring to FIG. 5, one may see in the magnified version of cursor line 45 that there might be a perceptible staircase in this line because one or more pixels composing the width of a line are laterally displaced from pixels composing the cursor in the next succeeding horizontal scan line. The step effect might be especially noticeable if the number of scan lines used to display the cursor are fewer than the total number of available horizontal scan lines.

With the new cursor generator it is easy to maintain high resolution or sharpness of angulated cursor lines without requiring a large number of locations in RAM 76. For the sake of contrast, image refresh memory 30 and graphics refresh memory 31 need to make many locations available. For example, as in a typical case, if each horizontal scan line for the image is comprised of 160 pixels and there are 160 scan lines in a frame, 160×160 or 25,600 one bit locations in image refresh memory 30 would be required. If the cursor memory, RAM 76, on the other hand, there are only two parameters for each horizontal cursor line component, namely, the X-position and width parameters for each line so for 160 lines there would be a requirement for 2×160 or 320 parameters and if each parameter is represented by eight bits and there are two parameters per line, the requirement is for 2560 bits of storage per cursor. But a 320-line raster is actually used. Here, for every image memory pixel there exists four addressable cursor memory 76 locations in the example which effectively results in a 640 horizontal element by 320 vertical element cursor display coordinate grid.

So to maximize resolution, the counters such as X-position counter 79 and width counter 78 are clocked at a rate for the cursor pixels which is four times the rate at which the image pixels are clocked or read out. As was mentioned early in this description, the image pixel clock pulse train is obtained by dividing the pulse train from master clock 116 in FIG. 1 by four. The undivided high speed clock is supplied directly from the master clock 116 by way of line 118 to the clock signal pins (CK) of the one or more pairs of X-position and width counters so they clock at the high rate. This effectively results in presenting four cursor pixels for every image pixel so that the staircase effect is obscured and a near vertical line appears more smooth to the naked eye. There may be some quantization in the vertical direction as a result of the limited number of lines but an improved result is obtained without enlarging RAM and software requirements. In summary, horizontal resolution can be raised to any extent by increasing the ratio of the counter pixel rate to the image pixel rate so each cursor pixel will result in the same ratio or multiple of cursor pixels per image pixel in each raster line.

In summary, it should now be evident that all of the advantages and new functional features set forth at the beginning of this description are achieved with a basic combination of a microprocessor, means for providing horizontal and vertical sync signals, a clock means for maintaining cursor and video information in synchronism, means for presenting cursor information on a line-by-line basis, a video signal mixer and operator interactive controls.

Although a preferred embodiment of the invention has been described in detail, this should be considered illustrative rather than limiting, for the underlying concepts can be implemented in other ways so the invention should only be limited as necessitated by construing the claims which follow.

We claim:

1. In a system including a video monitor having a display screen and a raster scanned image forming beam scanning the screen along a plurality of horizontal lines, said monitor having input means for video signals that are operative to control said beam to effect display of an image on said screen, means for superimposing one or more cursors on said display screen, comprising:

processor means, a readable memory coupled to said processor means for storing one or more programs usable by said processor means to generate parameters representative of the horizontal location and width of a segment in each horizontal raster scan line that contributes to defining the shape of the cursor to be displayed on said screen, random access memory means having an X-Y memory matrix for storing said horizontal location and width parameters for segments in the respective horizontal scan lines so that a sequence of said lines is capable of defining the cursor, operator interactive control means operatively coupled with said processor means and including a manually movable control member movable in X and Y directions, said control means responding to movements of said member by providing corresponding signals to said processor means, said processor means responding to said signals by generating parameters corresponding with a new position of the cursor on the display screen, means for causing said RAM to output said location and width parameters for segments in synchronism with the horizontal raster lines to which they respectively relate and means responding to said outputted location and width parameters by producing a signal for changing the intensity of said beam when it has scanned to the segment locating and for again changing the intensity of said beam when it has scanned the width of the segment, and mixer means having output means coupled to said input means of said video monitor and having first input means for said image video signals and second input means for said beam intensity changing signals.

2. In a system including a video monitor having a display screen and a raster scanned image forming beam for scanning the screen along a plurality of horizontal lines, said monitor having input means for video signals that are operative to control said beam to effect dispaly of an image on said screen, means for superimposing one or more cursors on said display screen, comprising:

processor means, a readable memory coupled to said processor means for storing one or more programs usable by said processor means to generate parameters representative of the horizontal location and width of a segment in each horizontal raster scan line that contributes to defining the shape of the cursor to be displayed on said screen, random access memory (RAM) means having an X-Y memory matrix for storing said horizontal location and width parameters for the respective horizontal scan lines so that a sequence of said lines is capable of defining the cursor, operator interactive control means operatively coupled with said processor means and including a manually movable control member movable in X and Y directions, said control means responding to movements of said member by providing corresponding signals to said processor means, said processor means responding to said signals by generating parameters corresponding with a new position of the cursor on the display screen, means for causing said RAM to output said location and width parameters for segments in synchronism with the horizontal raster lines to which they respectively relate and means responding to said outputted location and width parameters by producing a signal for changing the intensity of said beam when it has scanned to the segment location and for again changing the intensity of said beam when it has scanned the width of the segment, and mixer means having output means coupled to said input means of said video monitor and having first input means for said video signals and second input means for said beam intensity changing signals, another operator interactive control means operatively coupled with said processor means and including a manually rotatable control member rotatable about a single axis, said other control means responding to rotation of said rotatable member by providing signals indicative of its angle of rotation to said processor means, host computer (CPU) means, display controller means, input/output interface means coupling said CPU to said display controller means and to said processor means, respectively, said CPU being operative to provide data to said display controller for producing said image on said screen, said stored programs including a program for enabling said processor means to produce the parameters for a cursor comprised of a cursor line with a tick mark line intersecting it at a point designated as the isocenter, said processor means responding to said rotation indicative signals by rotating said parameters in fixed relationship with each other in said memory matrix for effecting rotation of said cursor line about said isocenter.

3. The device as claimed in claim 2 wherein:

said CPU is operative to produce a second set of parameters for storing in a part of said random access memory matrix, said second set of parameters being for a second fixed cursor line that is coincident with said aforementioned cursor line, such that when said aforementioned line is moved by operation of said manually movable control member of said interactive control means said aforementiond cursor line will remain at its original angle but will be parallel to said second fixed cursor line.

4. A cursor generator device for use with an image display system that includes a raster scanned video monitor having input means for video signals that control the monitor to display a picutre on its screen, a display controller including a memory matrix for storing signals corresponding to picture elements (pixels) in a horizontal line-by-horizontal line format, said display controller being operative to control conversion of said lines of pixel signals in succession to corresponding analog video signals for each horizontal raster line displayed on the screen, means for providing video control signals including horizontal and vertical sync and blanking pulse signals to said monitor, mixer means having output means coupled to the input means of said monitor and having plural input means one of which is for receiving the analog video signals from said display controller means and the other of which is for developing a visible cursor overlaying the picture on said screen, said cursor generator device comprising:

processor means, readable memory means for storing program information for controlling said processor means to generate parameters for defining one or more cursors to be displayed by said monitor, random access memory means coupled to said processor means and including a memory matrix for storing the parameters for defining an entire cursor, said matrix having a location for each horizontal raster line on which a part of said cursor is to appear intensifier on said display screen, the cursor parameters being stored in said matrix in successive horizontal lines corresponding with raster lines, one of the cursor parameters occuring in each horizontal line being for determining the X starting point position of a segment of the cursor defining line in a horizontal line and another of said parameters in the same horizontal line being for determining the width of said segment in said line, the parameters in the respective lines of the matrix determining the shape of the cursor, operator interactive control means coupled to said processor means and including a manual member movable to provide signals to the processor means corresponding to the desired X and Y coordinates of the cursor, said processor means responding to movement of said manual member by providing corresponding cursor parameters to said memory matrix for producing the cursor at corresponding coordinates on the display screen, and counter means for determining the starting point and width of each segment and means responding to occurrence of successive ones of said horizontal blanking pulse signals by presenting the parameters from said memory matrix for a line corresponding to a raster line to said counter means, said counter means responding to said parameters by causing one signal to be produced and fed to an input of said mixer means when the starting point for a cursor line segment in the horizontal scan line is determined, occurrence of said one signal altering the intensity of the display on the line and by causing another signal to be produced and fed to said mixer means when the width of the segment is determined for discontinuing said altering.

5. The cursor generator as claimed in claim 4 wherein program information stored in said readable memory means includes information for generating a cursor comprising a straight line and a tick mark intersecting it, the point of intersection being designated an isocenter, said operator interactive control means including a manually operable switch means operable to provide signals to said processor indicative of the desired rotational angles of the cursor line on the screen, said processor responding to said signals by providing the cursor parameters to said random access memory for producing a correspondingly angulated cursor line on the screen which cursor line is rotated about said isocenter.

6. The cursor generator as claimed in claim 5 and a host computer coupled to said display controller for supplying image pixel signals to it and means for coupling said host computer to said processor and said random access memory and said operator interactive means, said host computer being operative to provide said processor with data specifying the X and Y coordinates and the angle of the original cursor presently on the screen and said processor responding by providing a set of parameters to said random access memory for producing a correspondingly positioned stationary second cursor line on said screen such that said original cursor line may be moved and maintained in parallelism with said second cursor line by operation of said manual member of said operator interactive control means.

7. The image display system as in claim 4 wherein:

said means responding to occurrence of successive ones of said horizontal blanking pulses comprises a direct memory access controller operative in response to said pulses, respectively, to enable said counters for being loaded with the cursor parameters for a raster line corresponding to the pulse.

8. The system as claimed in claim 7 wherein said random access memory means comprises two partitions, one of which holds the parameters for the cursor presently being displayed on said screen and the other of which holds the data for the same cursor configuration but for a new cursor position resulting from said operator interactive control being operated, and means for coupling said vertical blanking pulses to said processor, to enable said processor to generate the parameters for new positions of said cursor and transfer said parameters to successively alternate ones of said partitions during existence of said vertical blanking pulses.

9. In a computerized tomography system including means for producing signals representative of picture elements (pixels) for enabling display of preliminary and axial type x-ray pictures, respectively, of a body on a raster scanned video monitor including a display screen and an image forming beam for scanning the screen along a plurality of horizontal lines, a display controller having a memory matrix for storing said pixel signals in an X-Y format and for being clocked to read out said pixel signals in succession in each horizontal line corresponding with a horizontal line in the raster, means for converting said pixel signals in successive lines to corresponding analog video signals, mixer means having an output coupled to said monitor and having a plurality of inputs one of which is for receiving said analog video signals, means for providing pixel clock signals and horizontal and vertical and blanking pulse signals for controlling said monitor, and means for producing a cursor defined by segments in raster scan lines having distinctive brightness intensity for being overlayed on the picture displayed on the screen comprising:

a processor and address and data buses to which said processor is coupled, a readable memory coupled to said buses, said memory being operative to store data representing one or more programs for controlling said processor to generate cursor defining parameters for the segment of a cursor in each horizontal scan line that contributes to composing the complete cursor to be displayed on said screen, a random access memory (RAM) coupled to said address and data buses for being supplied by said processor with all of the parameters for producing a particular cursor on said screen, said memory having a location for each horizontal scan line used for developing the cursor on the screen, counter means having input means coupled to said data bus for receiving data representative of said parameters and having means for receiving load signals which clock loading of said counters with the parameters for defining the starting point and width of a segment within the horizontal raster line to which the segment relates, operator interactive control means coupled with said processor and operative to place the cursor at the desired location and orientation on the screen, said processor responding to signals from said operator interactive means by placing the cursor parameters in the RAM for achieving correspondence with said cursor location on the display screen, a direct memory access (DMA) controller having a plurality of signal output ports coupled respectively to said load signal receiving means of said counter means, said DMA controller responding to occurrence of successive horizontal sync pulses by causing said processor means to isolate from said bus means and to provide load signals for parallel loading data representative of the cursor parameters for the horizontal line to which said pulse relates from the RAM into said counter means, and means responsive to said counter means using one of said parameters to determine the starting point of a cursor segment in a horizontal scan line by providing a signal to an input of said mixer means for altering the intensity of said horizontal line on said screen and responsive to said counter means using another of said parameters to determine the width of said line by discontinuing said intensity altering signal to the mixer means.

10. The apparatus as claimed in claim 9 wherein said counter means comprises a segment position determining counter and a width determining counter cooperating as a pair and said RAM memory has two similar partitions of memory for each position and width counter pair, each of said partitions being for storing the parameters for a complete cursor, said counters obtaining parameters from one partition for the cursor being currently displayed in one position while said processor means is providing said RAM with a new set of parameters for cursor position update that may be required as a result of said operator interactive control means, means for switching said counters alternately for receiving cursor defining parameters from one to the other of said partitions in response to occurrence of vertical blanking signals such that no cursor discontinuities are apparent on the display as a result of cursor position update.

11. The apparatus as claimed in claim 9 wherein said computerized tomography system includes an x-ray source and detector means spaced apart to dispose a body between then to obtain data for producing axial views of body layers, means for supporting said source and detector means for tilting in a common plane about a transverse axis to enable obtaining axial views of body layers at an angle corresponding with the angle of tilt about said axis, means for positioning a body and for obtaining relative longitudinal translation of said body along a line perpendicular to said axis between a body and said source and detector means to obtain data for producing a preliminary x-ray picture, one of said programs causing said processor to provide to said RAM the parameters for producing a cursor comprising a long line with a tick mark intersecting it while said preliminary view is being displayed on said screen, said operator interactive controls being operative to move said tick mark along said line and to change the angle of said line on said screen so that the operator can place said line at the angle at which axial views of the body are desired, a host computer (CPU) coupled to said bus means and operative to determine the angle of said line and to produce signals indicative of the angle to which said x-ray source and detector supporting means are to be tilted for obtaining axial views at a corresponding angle.

12. The apparatus as in claim 11 wherein said CPU is operative to determine the location of the point where said tick mark intersects said line and responds to such determination by effecting relocation of said body such that said transverse axis extending through the body will correspond with the point of rotation of the line on the preliminary view being displayed to thereby obtain isocentric angulation of the axial planes.

13. The apparatus as claimed in claim 12 wherein said CPU is operative to provide cursor defining parameters corresponding with the cursor defining data provided by said processor to effect display of a corresponding and coincident cursor line on the screen, said cursor line produced by said processor then being movable in parallelism with the cursor produced by said CPU in response to operation of said operator interactive control means.

14. The apparatus as claimed in any one of claims 9, 10, 11, 12 or 13 including means for clocking said counters at a rate higher than said image pixel clock rate to thereby improve the resolution of the lines composing the cursor.

* * * * *

UNITED STATES PATENT AND TRADEMARK OFFICE
CERTIFICATE OF CORRECTION

PATENT NO. : 4,259,725
DATED : March 31, 1981
INVENTOR(S) : Edward W. Andrews; James E. Blake; Thomas Lambert It is certified that error appears in the above—identified patent and that said Letters Patent is hereby corrected as shown below:

Claim 1, Column 16, Line 18 --(RAM)-- should be inserted between memory and means Claim 1, Column 16, Line 38 "locating" should read --location--

Claim 2, Column 16, Line 50 "dispaly" should read --display--

Claim 4, Column 17, Line 59 "picutre" should read --picture--

Claim 11, Column 20, Line 59 "then" should read --them--

Signed and Sealed this

Twenty-eighth Day of July 1981

[SEAL]

Attest:

GERALD J. MOSSINGHOFF

Attesting Officer

Commissioner of Patents and Trademarks